United States Patent [19]

Malmqvist et al.

[11] Patent Number: 4,833,093

[45] Date of Patent: May 23, 1989

[54] METHOD OF SILANIZATION OF SURFACES

[75] Inventors: Magnus Malmqvist, Upsala; Göran Olofsson, Umeå, both of Sweden

[73] Assignee: Forsvarets Forskningsanstalt, Stockholm, Sweden

[21] Appl. No.: 111,152

[22] Filed: Oct. 21, 1987

Related U.S. Application Data

[63] Continuation of Ser. No. 545,378, filed as PCT SE83/00027 on Jan. 27, 1983, published as WO83/02669 on Aug. 4, 1983, abandoned.

[30] Foreign Application Priority Data

Jan. 27, 1982 [SE] Sweden ............................ 8200442

[51] Int. Cl.[4] ..................... G01N 33/552; C12Q 1/68; C23G 16/00; B08B 7/00
[52] U.S. Cl. ................................. 436/527; 427/255.6; 436/828; 435/6; 435/7; 134/42
[58] Field of Search ............... 436/527, 828; 435/174, 435/176, 6, 7; 427/3, 255.6; 134/42

[56] References Cited

U.S. PATENT DOCUMENTS

| | | | |
|---|---|---|---|
| 3,276,853 | 10/1966 | Eakins | 65/3 |
| 3,519,538 | 7/1970 | Messing | 260/112.5 R |
| 3,652,761 | 3/1972 | Weetall | 436/527 |
| 3,831,432 | 8/1974 | Cox | 73/23 |
| 3,924,032 | 12/1975 | Hertl | 427/220 |
| 4,046,870 | 9/1977 | Hertl et al. | 436/500 X |

FOREIGN PATENT DOCUMENTS

| | | |
|---|---|---|
| 1130228 | 8/1982 | Canada . |
| 0073980 | 3/1983 | European Pat. Off. . |
| 53-83604 | 7/1978 | Japan . |
| 1486826 | 9/1977 | United Kingdom . |
| 1512052 | 5/1978 | United Kingdom . |

OTHER PUBLICATIONS

Buzek et al, Stoichiometry and Kinetics of the Reaction of Silica with Organosilicon Compounds, Journal of Colloid and Interface Science, vol. 79, No. 1, Jan. 1981, pp. 47–55.

Hertl, Mechanism of Gaseous Siloxane Reaction with Silica I., The Journal of Physical Chemistry, vol. 72, No. 4, Apr. 1968, pp. 1248–1253.

Hertl, Mechanism of Gaseous Siloxane Reaction with Silica II., The Journal of Physical Chemistry, vol. 72, No. 12, Nov. 1968, pp. 3993–3997.

Methods in Enzymology (Klaus Mosbach, Ed.), vol. 44, 1976, Academic Press, pp. 134–149.

Sagiv, Organized Monolayers by Adsorption. 1. Formation and Structure of Oleophobic Mixed Monolayers on Solid Surfaces, Journal of the American Chemical Society, vol. 102, Jan. 2, 1980, pp. 92–98.

Handbook of Thin Film Technology (Leon I. Maissel & Reinhard Glang, Eds.), 1970, McGraw-Hill Book Company, pp. 6-37 to 6-42.

(List continued on next page.)

Primary Examiner—Johnnie R. Brown
Assistant Examiner—Jeremy M. Jay
Attorney, Agent, or Firm—Fleit, Jacobson, Cohn & Price

[57] ABSTRACT

The present invention relates to a method of silanizing surfaces for use in detecting organic molecules and biomolecules by means of surface-sensitive detection methods. The molecules to be detected become covalently bonded to the solid, plane test surface which contains, by means of silanization, groups which are functional for the covalent bonding. The invention relates to a silanization technique, which combines a special cleaning technique for the surfaces to be silanized and a silanization process at a low pressure and with the silane in gas phase and at an enhanced temperature of the surfaces to be silanized. The method gives reproducible surfaces provided with stable, homogeneous and functional silane layers of mono-layer character. The surfaces are then used for covalent coupling of highly specific organic molecules and biomolecules to the surfaces. The coupling may be carried out directly by means of a reactive group on the silane or by means of a bifunctional coupling reagent, such as N-succinimidyl-3-(2-pyridyldithio)-propionate, carbodiimide or glutardialdehyde.

15 Claims, 3 Drawing Sheets

OTHER PUBLICATIONS

Janata et al., Chemically Sensitive Field Effect Transistors, Ion–Selective Electrodes in Analytical Chemistry (H. Freiser, Ed.), vol. 2, 1980, pp. 107–172.

Bascom, Structure of Silane Adhesion Promoter Films on Glass and Metal Surfaces, Macromolecules, vol. 5, No. 6, Nov.–Dec. 1972, pp. 792–798.

Mittal et al., Vapor Deposited Silanes and Other Coupling Agents, J. Adhesion, 1976, vol. 8, pp. 93–97.

Haller, Covalently Attached Organic Monolayers on Semiconductor Surfaces, Journal of the American Chemical Society, vol. 100, Dec. 20, 1978, pp. 8050–8055.

Carlsson et al., Protein Thiolation and Reversible Protein–Protein Conjugation, Biochem. J. (1978), vol. 173, pp. 723–737.

Tadros et al, Adsorption of Potential–Determining Ions at the Silica Aqueous Electrolyte Interface and the Role of Somecations, J. Electronal. Chem., vol. 17 (1978), pp. 267–275.

Chemical Abstracts, vol. 92 (1980), abstract No. 90 298e, Biophys.–Struct. Mech. 1979, 6(1) 67–80 (Eng.).

Chemical Abstracts, vol. 93 (1980), abstract No. 91 093s, J. Appl. Biochem. 1979, 1(5–6), 442–7 (Eng.).

Chemical Abstracts, vol. 91 (1979), abstract No. 188 710n, Sb. Nauchn. Tr., Vses. Nauchno–Issled. Inst. Lyuminoforov Osobo Chist. Veshchestv. 1978, 17, 90–4 (Russ.).

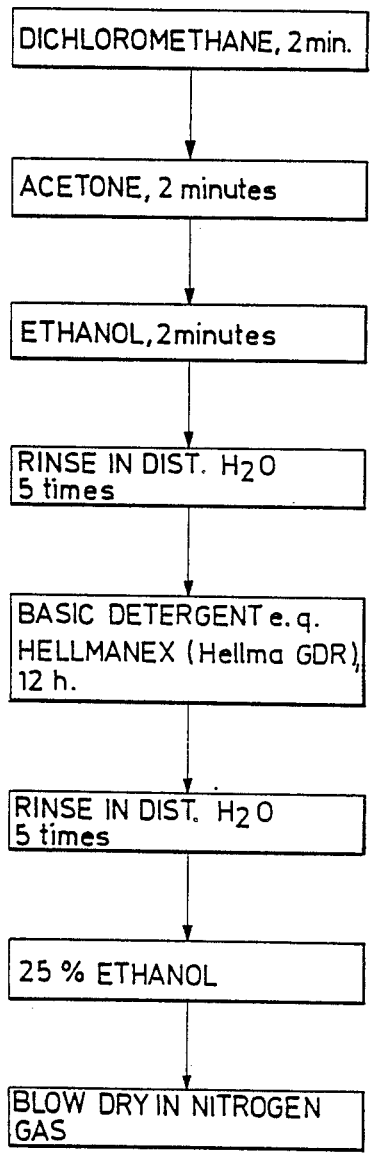

METHOD OF SILANIZATION OF SURFACES

This application is a continuation, of application Ser. No. 545,378, filed as PCT SE83/00027 on Jan. 27, 1983, published as WO83/02669 on Aug. 4, 1983, abandoned.

The present invention relates to an improved method of silanization of surfaces for use in detecting organic molecules or biomolecules, e.g., proteins.

Biomolecules may be detected by utilizing the biospecificity between two or more different molecules. The reaction product thus obtained may then be determined and measured in a number of different ways. The most common detection methods used today are based on some kind of labelling, for instance with an enzyme or radioactive isotopes, of one or more of the measuring system components. Such methods are time-consuming, require costly and relatively complicated equipment, are not suitable for automation, and the use of radioactive isotopes is not preferred for working environment reasons.

In surface-sensitive detection methods, the labelling of the components is eliminated, and the reaction product obtained is measured directly. Examples of detection methods of this kind are ellipsometry and simplified variants thereof (Ellipsometry and Polarized Light, Azzam, R. M. A. and Bashara, N. M., North Holland Publ., Amsterdam, 1977); chemically sensitive field-effect transistor, so-called CHEM-FET (Theory, Design and Biomedical Applications of Solid State Chemcial Sensors, Cheung, P. W., Flemming, D. G., Neuman, M. R. and Ko, W. H. (eds.), CRC Press Inc., 1977); and other electrochemical detection systems, such as measurement of differential capacitance and potential changes.

The advantages of the surface-sensitive detection methods are their simplicity, rapidity and low cost. Characteristics which these surface-sensitive detection methods have in common, and which distinguish them from conventional detection methods, are the fact that they measure the average change at the surface of some physical-chemical parameter, e.g., the quantity per surface unit, the change of the charge per surface unit, and that the change can be measured continuously. These characteristics are essential conditions for miniaturization, rapidity and accuracy, since kinetic parameters can be measured. Moreover, the test surface can be made very small, which considerably reduces the consumption of the biomolecules present in the measurement system.

The test surface is a solid, plane surface of a magnitude of some mm$^2$ down to $10^{-3}$mm$^2$ with reproducible physical-chemical surface qualities, e.g., surface energy, optical refractive index, electric potential. The quantities of the bulk material are dependent on the measurement principle (e.g., ellipsometry-light reflecting, CHEM-FET semiconductors, electrochemical measurement principles—electrically conducting or semiconductors).

In the simplest example of measuring a biospecific reaction, e.g., an immunochemical reaction, one component is adsorbed to the surface. However, the adsorption of biomolecules causes problems with the sensitivity and specificity of said methods. Adsorbed molecule films are never completely stable in a liquid phase but, to a certain extent, are in a dynamic equilibrium with other molecules present in the liquid. Besides, an adsorption process is very difficult to control, and reproducible molecule films, as far as biological activity and physical-chemical qualities are concerned, are difficult to obtain. Biomolecules, especially proteins, are generally adsorbed irreversibly to surfaces, resulting in expendable systems and making automation more difficult.

The present invention relates to a method for the treatment of the test surface in such a manner that the bio-specific molecules will become covalently bonded to the surface in a reproducible and well-controlled manner, so that surface-sensitive detection methods can be utilized. The characteristics of the invention are evident from the patent claims.

Thus, the test surface is a reproducible, solid, plane surface which is chemically modified by means of the silanization process of the invention, in that the test surface is given reactive groups suitable for the covalent bonding. Examples of such surfaces are oxides or oxide-coated metals, semiconductors and insulators, e.g., Si/SiO$_x$, Si/Si$_3$N$_4$/Si$_3$N$_4$O$_x$, Ti/TiO$_x$, Pt/PtO$_x$, Pd/PdO$_x$, Al/AlO$_x$, Ni/NiO$_x$, x means here that the stoichiometry of the oxide does not necessarily need to be well-defined.

It has previously been possible to produce oxide-coated surfaces having reproducible physical-chemical qualities. These oxide-coated surfaces have hydrated hydroxyl groups on the surface after a suitable cleaning procedure, but said groups per se are not suitable for the direct covalent bonding of other molecules. It is known that the surface can be chemically modified by the use of a reaction with an organosilane or an alcohol (P. F. Cox, U.S. Pat. No. 3,831,432 (1974)). Methods have been devised to modify the hydroxyl groups into chloride groups (W. Hertl, U.S. Pat. No. 3,924,032 (1975)), and possibilities are mentioned for reacting with thionyl chloride or the direct condensation of carboxyl or hydroxyl groups in the biomolecules with the surface (T. Chiyou, Japanse Appl. No. 53-83604 (1978)). Stability in the water phase for surfaces that have been modified by these methods is only expected for the reactions with organosilanes. This is because the Si—C bond has higher hydrolytical stability than the O—C bond which is the result of the other modification techniques.

Organosilanes are of three main kinds: chlorosilanes, alkoxylsilanes and silasanes. They can be obtained as mono-, di- or trifunctional. Reactions between said silanes and oxide-coated surfaces have been studied in detail, and a number of reaction conditions are known. The majority of said studies are concerned with porous or solid pellets or spheres of small size; and it is known that the pretreatment of the spheres or the pellets and the temperature and the time for the reaction are critical parameters (see, for instance, W. Hertl, J. Phys. Chem., 72 (1968), 1248, and F. Buzek and J. Rathousky, J. Colloid Interface Sci., 79 (1981), 47. On the other hand, the silanization of solid, plane surfaces has not attracted attention to the same extent.

On plane surfaces the reproducibility, homogeneity and stability of the reaction can be studied in simple ways. The most common method of silanizing surfaces is to let the reaction between the surfaces and organosilanes occur in liquid phase (Mosbach K. (ed.), Methods in Enzymology, Vol. 19, pages 139–140, Academic Press, N.Y., 1976). It is known that the presence of water in the systems will cause polymerization of the silane, resulting in heterogenous and unreproducible silane layers. (See, for instance, W. D. Bascom, Macromolecules, 5 (1972), 792). Strictly waterfree reaction conditions are complicated to achieve and technically difficult to control. Besides, the presence of previously more or less polymerized silanes cannot be completely eliminated in a reaction in liquid phase. It is also known that the reaction between chlorine and alkoxysilanes and the oxide surfaces will occur at an appreciable speed only at higher temperatures (150°–400° C.) (F. Buzek and J. Rathousky, J. Colloid Interface Sci., 79 (1981), 47).

Said conditions are difficult to obtain with a reaction in liquid phase. This problem can be eliminated by vacuum distillation of the silane and bringing the surfaces in contact with the silane in the gas phase (e.g., K. L. Mittal and D. F. O'Kane, J. Adhesion, 8 (1976), 93). However, with a reaction at room temperature, no water-stable layers are obtained (I. Haller, J. Am. Chem. Soc., 100 (1978), 8050). A method to silanize fibre glass in the gas phase at an enhanced temperature has been described (J. Eakins, U.S. Pat. No. 3,276,853 (1966)). However, said method is specialized for fibre glass and, in the described embodiment, it is not suitable for the silanization of the surfaces here described. Besides, the process is carried out at atmospheric pressure and in contact with the ambient air.

However, if the surface modification is carried out according to the method of the present invention, the reproducible and stable silane layers are obtained which are required for the instrumental detection of organic molecules, such as biomolecules, using surface-sensitive detection methods. The present invention combines special cleaning procedures for the solid, plane surfaces with a low pressure distillation of the silane over to a vessel comprising the oxide-coated surfaces, the oxide-coated surfaces being kept at an enhanced temperature suitable for the reaction between the organosilane and the surface, such as 75°–250° C., and preferably 100°–200° C.

The cleaning procedures will free the surfaces from organic and inorganic contaminations and will give the surfaces a hydrophilic character. The procedure described in example 1a preferably can be used for test surfaces that are part of a bulk material, such as the surface of single crystal silicon or foils of titanium. Test surfaces consisting of thin films coated on a bulk material of, for instance, glass or plastic require a milder cleaning program (example 1c), and those programs must be adapted to the special surface.

The distillation of the silane will make sure that no polymerized silanes will leave the silane solution and come into contact with the surfaces. Since the process is carried out at a low pressure and at an enhanced temperature, the amount of free water in the system is minimized, which reduces the risk of polymerizing the silanes when they are in the gas phase. Moreover, a mold treatment of thermally unstable silanes is made possible because of the boiling point depression. Keeping the surfaces at a temperature required for the reaction ensures that the silanes react covalently with the surfaces and form a water-stable modified surface. The temperature of the surfaces is, however, not enhanced so much that the water that is bonded to the surfaces completely disappears. The bonded water, together with the water that is left in the system, makes possible hydrolysis of the silane before the reaction with the surface hyrdoxyl groups can occur. The temperature is so chosen that an optimal result is obtained with respect to reproducibility, stability and functionality of the modified surfaces. The time during which the silanization occurs is also a variable parameter.

The surfaces that are silanized with said technique are reproducible and give polymer-free silane layers of monolayer or submonolayer character (verified with contact angle measurements, ellipsometry, scanning transmission electron microscopy and electron spectroscopy for chemical analysis). The surfaces are functional and stable in an environment comprising water of a different pH, which can be verified by coupling chemically reactive gel beads to the surfaces (example 4). A suitable method of examining the presence of reactive, functional groups on a silanized surface is to modify gel beads with organic molecules and bring them together with the surface. If functional groups are present on the surface, the gel beads are bonded covalently and specifically to the surface.

There also can be bonded to the reactive groups either a spacer (i.e., a molecule that brings the biomolecule out a certain distance from the surface and thus prevents the molecule from being affected by the surface in a manner detrimental to the detection system), or a combination of spacer and inert molecules (i.e., molecules that do not take part in the biospecific reaction but, for instance, prevent an unspecific adsorption to the surface), giving an environment that is physically-chemically favorable to the bonded molecule, such as by being hydrophilic. The biospecific molecules may also be bonded directly to the reactive groups on the surface.

The covalent bonding of organic molecules or biomolecules to reactive groups on the test surface, e.g., amino, thiol, epoxy, vinyl, pyridyldisulfide, succinimide, carboxyl, methoxy, ethoxy or methacryl, may be carried out with bifunctional coupling reagents, e.g., with glutaraldehyde, carbodiimide or N-succinimidyl-3-(2-pyridyldithio)propionate (SPDP, Pharmacia Fine Chemicals, Uppsala, Sweden). This may be done by a direct bond between the reactive group and the desired molecule, or via a link in-between, a so-called spacer. This link or the direct bond may be cleavable under conditions which do not disturb the bonding of the reactive group to the test surface, e.g., by reduction of the disulfide structure or thioldisulfide interchanges, oxidation of vicinal diol structures with periodate or enzymatically cleavable groups, such as esters or glycoside bonds.

By coupling with SPDP, intramolecular couplings are eliminated, which results in monolayers of the molecules bonded to the surfaces.

In order to eliminate modifications of organic molecules or biomolecules in solution, the bond to the test surface is achieved by directly inserting reactive groups on the test surface, e.g., N-hydroxysuccinimide ester or epoxides. This is done by modifying said reactive groups, as is evident from example 3, or by direct synthesis of a silane so that it is directly given reactive groups.

The invention may be exemplified as follows:

a. Spontaneously oxidized silicon is cleaned according to FIG. 1a. The surfaces that are blown dry in nitrogen gas are then kept at 150°–180° C. and are silanized at a low pressure in gas phase with a silane (e.g., A-189 from Union Carbide) which modifies the surface so that thiol groups are introduced. These thiol groups on the silicon surface are modified with SPDP (N-succinimidyl-3-(2-pyridyl-dithio)propionate) in an acetate buffer at pH 4.5 because of the thioldisulfide interchange reactions that occur. N-succinimidyl, which is introduced on the silicon surface in this way, can react and bond amino-containing compounds, e.g., protein, at a higher pH.

b. The silicon surfaces are silanized as under a. Amino-containing organic molecules or biomolecules are modified with SPDP and can then be bonded to the thiolsilanized surface via thioldisulfide interchange reactions.

c. The silicon surfaces are silanized with an amino group introducing silane (e.g., A 1120 from Union Carbide) as under a. The amino groups introduced on the silicon surface are modified with SPDP in the same way as the amino-containing molecule. One part is reduced to thiol, and the covalent bonding occurs via thioldisulfide interchange reactions.

d. The silicon surfaces are silanized as under c. Carboxyl-containing molecules are coupled to the surface by means of carbodiimide reagents, e.g., 1-cyclohexyl-3-(2-morpholinoethyl)-carbodiimide-metho-p-toluenesulfonate or N,N'-dicyclohexylcarbodiimide.

e. The silicon surfaces are silanized as under c. Amino-containing molecules are coupled to the surface by means of glutaraldehyde.

f. The silicon surfaces are silanized with an epoxy-introducing silane (e.g., A 187 from Union Carbide) as under a. The epoxy-modified silicon surface can then covalently bond amino-containing, thiol-containing or hydroxyl-containing molecules.

g. The silicon surfaces are silanized with mixtures of silanes so that multifunctional surfaces are formed on the silicon. These different functional groups can be used to bond different molecules described under a.–f.

h. Silicon is silanized with a N-succinimidyl-introducing silane as under a. The N-succinimidyl-modified silicon surface can then covalently bond amino-containing organic molecules or biomolecules.

i. Silicon is silanized with a pyridyldisulfide-introducing silane as under a. The pyridyldisulfide-modified silicon surface is then reduced in water phase with, e.g., dithiothreitol, which introduces free SH-groups on the surface. These can be covalently bonded to SPDP-modified organic molecules or biomolecules.

j. Silicon coated with silicon nitride is cleaned according to a. and silanized according to a.–i.

k. Titanium is evaporated or sputtered onto glass surfaces to a thickness of 500–10,000 Å, is cleaned according to FIG. 1b, and is silanized according to a.–i.

l. Machined titanium is cleaned and silanized according to a.–i.

The characteristic of the surface-sensitive detection methods to register the average changes on the test surface has as a result that, in contact determinations, the magnitude of the signal is a measure of the surface concentration of the substance that is bonded to the surface, while conventional solid phase methods, such as RIA and ELISA, measure the amount of the substance that is bonded to the surface, independent of its size. The consequence of this different is that the test surface can be miniaturized and, thus, the sample volume and the amount of the substance coupled to the test surface is reduced.

Another effect of the difference between measuring, for instance, a radioactive disintegration and determining the qualities of surfaces is that, of necessity, attempts should be made to utilize every part of the surface for the coupling of specifically active molecules. Every molecule coupled to the surface should have the desired specificity and be orientated in such a way that the molecule is not sterically hindered from taking part in its specific interaction. This means that every substance that is coupled to the surface should have as high a purity as possible.

For biospecific systems based on immuno reactions, it is essential to change over from serum antibodies, being a mixture of inactive and active antibodies, to purified antibodies or hybridoma antibodies. Serum antibodies can be purified by affinity chromatography, and the antibodies obtained in such a way are all directed towards the same antigen. However, purified serum antibodies react with different parts of the antigen and have different equilibrium constants.

Monoclonal antibodies or hybridoma antibodies have the characteristic of being antibodies with only one specificity and one equilibrium constant. If there antibodies are coupled to the test surface, a more uniform surface is obtained, having an affinity for the antigen and where all antibodies on the surface can bind their antigens. This is an essential contribution in order to increase the resolution and the sensitivity of the measurement methods, which is not apparent from earlier patents and publications referring to surface-sensitive detectors.

Monoclonal antibodies can be produced against a very large number of different antigens in low and high-molecular organic compounds. This means that, by using assay methods based on a surface-sensitive detection technique with monoclonal antibodies bonded to the surface, low-molecular substances can be measured, such as hormones and substances that are toxic and dangerous to the environment, and high-molecular substances, such as proteins, polysaccarides, nucleic acids, viruses or bacteria. Optical and electrical methods give different sensitivities, depending on the size and charge of the antigen and its ability to induce potential changes on the test surface.

Enzymes are proteins that catalyze a chemical reaction. Many substances that are toxic and dangerous to the environment act by inhibiting enzymes and specifically binding to the active surface. This presents the possibility of selectively measuring enzyme inhibitions by covalently binding the enzyme to the test surface and then measuring the change that will occur when the inhibitor is bound to the enzyme.

Determinations of the amount of an enzyme can be carried out either by means of enzyme activity measurements or by means of conventional immunological methods which, however, will not give any information about the enzyme activity. By coupling a specific enzyme inhibitor covalently to a plane test surface, the enzyme content can be measured by means of surface-sensitive detection methods because of the bonding of the enzyme to the inhibitor on the solid phase.

Protein A from *Staphylococcus aureus* is a protein that can bind immunoglobulins from several different species in its Fc-part. Every Protein A molecule has several bonding sites, and the protein is often used to detect immunoglobulins in methods for measuring the amount thereof and microscopic section-cuttings. By covalently coupling Protein A to plane test surfaces, the IgG-content of samples can be measured, as is evident from example 2b.

The example shows that it is essential that every molecule coupled to the surface takes an active part in the biospecific reaction in order to obtain as high a surface concentration as possible. Protein A also has the ability to orient the antibodies so that the antigen-bonding structures of the antibodies will be exposed out into the solution by binding to the Fc-part of the immunoglobulin. This ability can be utilized to increase the efficiency of the antigen-antibody reaction.

The bond between Protein A and the Fc-part of the immunoglobulin is cleavable at a low pH (example 2b). This can be used to regenerate the test surface. The bond between the immunoglobulin and an antigen is, in general, also cleavable at a low pH. In those cases where antibodies have been oriented by means of Protein A on the test surfaces, the cleavage between said molecules can be prevented by means of mild cross-linking of Protein A and the antibodies (e.g., with glutardialdehyde). When rinsing in a low pH (2-3), only the bond between the antibody and the antigen is cleaved, and the test surface can be used again.

Moelcules that may be coupled to the test surface after the surface modification according to the invention are, for instance, antibodies, preferably monoclonal antibodies, antigens, Protein A from *Staphylococcus aureus*, enzymes, nucleic acids, enzyme inhibitors and enzyme substrates. Examples of the detected substance are antigens, antibodies, nucleic acids, enzymes, enzyme inhibitors and enzyme substrates, as well as larger complexes such as viruses and microorganisms.

The invention will now be described in more detail in the following examples, with reference to the attached drawings, where FIG. 1a shows the cleaning procedure suitable for use on the surface of a bulk material;

□, cleaned surfaces

○, surfaces that have been exposed to the silanization procedure but without the addition of silane ▽, aminosilanized surfaces ■, aminosilanized surfaces that have been modified with SPDP ●, aminosilanized surfaces that have been modified with SPDP and reduced with dithiothreitol. A covalent bonding of the molecules to said surfaces is expected to occur.

The symbols give the average values of two separate experiments.

Figure 4:
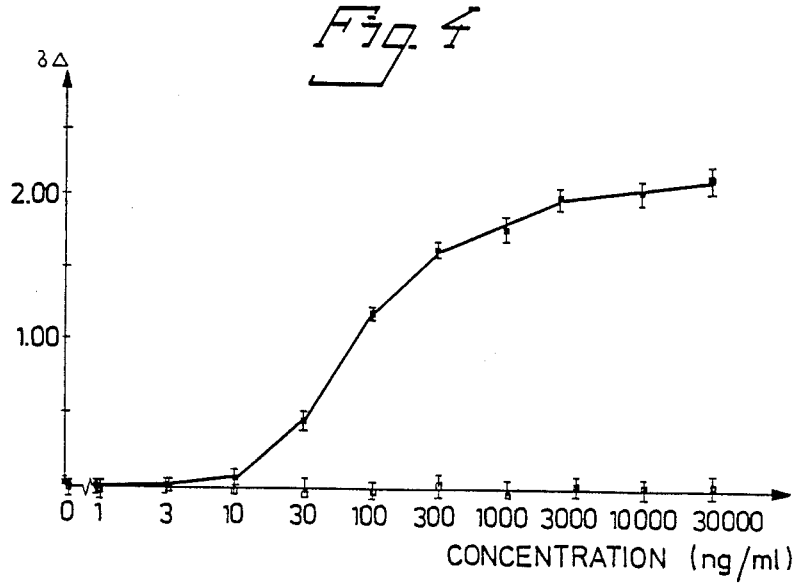

FIG. 4 is a diagram visualizing the interaction of immunoglobulin G from rabbit with Protein A (pA), covalently bonded to silicon surfaces, and the meanings of the symbols used are:

■, interaction of immunoglobulin G with Protein A

□, the same surfaces after being cleaned at a low pH

EXAMPLE 1A

Introduction of amino groups on hydrophilic single crystal silicon.

Figure 1A:
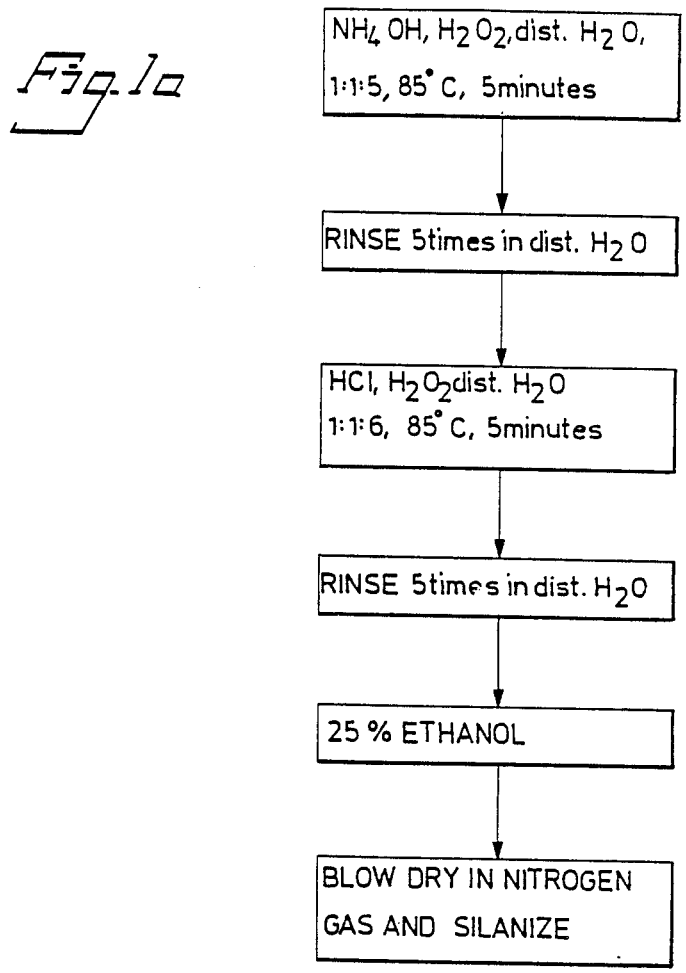
FIG. 1b shows a milder cleaning procedure at room temperature suitable for use on a surface that consists of a film disposed on a bulk material.

Single crystal n-doped silicon (Wacker Chemitronic, West Germany) is cut into $5 \times 5$ mm pieces and cleaned according to the method shown in FIG. 1a. The silicon is hydrophilic after this treatment, with a critical surface tension of about 39 dynes/cm, a polar contribution of about 50 dynes/cm, and a dispersion contribution of about 19 dynes/cm, measured by means of contact angle measuring.

Figure 2:
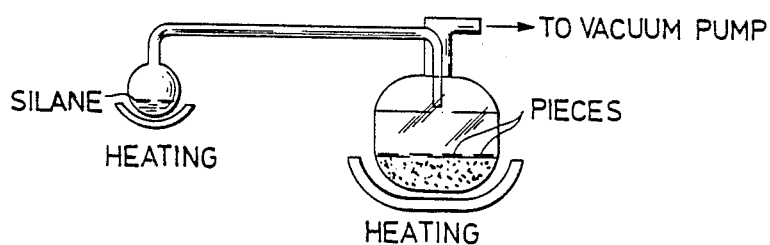
FIG. 2 shows a suitable embodiment of the silanization equipment.

The silanization is carried out in the apparatus shown in FIG. 2. All parts of the apparatus are made of glass, with silicone grease being placed in the joints. The silicon pieces, blown dry in nitrogen gas, are put into the vessel on the right, which is kept at a temperature of about 160° C. In the left vessel, some mls of N-$\beta$-(aminoethyl)-$\gamma$-aminopropyl-trimethoxysilane (Union Carbide, A-1120) are poured, the N-$\beta$-(aminoethyl-$\gamma$-aminopropyl-trimethoxysilane having been distilled once before use. The system is evacuated to about 0.1 torr and is kept in this condition for 3-4 h, during which the water of the system partly disappears. Then, the silane is vacuum distilled over into the vessel on the right by raising the temperature of the left vessel to about 85° C. The silicon pieces are maintained the entire time of about 160° C., and the silanization is now carried out during 2-4 days. Then, the vacuum distillation of the silane is stopped, and the system is maintained for about another 12 h at an enhanced temperature and low pressure, after which the heating is stopped and the system is allowed to cool down while maintaining the vacuum. Finally, the system is filled with dried air and the pieces are removed.

The aminosilanized pieces are reproducible after this process and have a silane coating of submonolayer character (verified by means of electron spectroscopy for chemical analysis and ellipsometry). The surfaces are homogeneous and contain no silane polymers (scanning transmission electron microscopy). Furthermore, the surfaces have functional amino groups as determined by contact angle measurement and gel bead test (see example 4), that are stable in water at pH 1 to pH 11 (gel bead test (see example 4).

EXAMPLE 1b

Introduction of sulfhydryl groups on hydrophilic, single crystal silicon.

Silicon is cleaned according to example 1a and silanized with $\gamma$-mercaptopropyl-trimethoxysilane (Union Carbide, A-189). The silanization is carried out according to example 1a, but with the difference that the silane temperature during the vacuum distillation is 25°-35° C.

The sulfhydrylsilanized pieces are characterized according to example 1a with a similar result.

EXAMPLE 1C

Introduction of amino groups on Ti/TiO$_x$-films.

Electrodes can be made of thin metal or semiconductor films. These films are coated on some suitable substrate, e.g., glass or plastic. In the present example, titanium was evaporated in a 3000 Å thick film on glass surfaces. For these thin films, a milder cleaning program had to be used than the method described in example 1a. The titanium-coated glass surfaces were cleaned according to the method shown in FIG. 1b. The pieces have a hydrophilic surface structure after this treatment. The surfaces were then silanized according to example 1a.

EXAMPLE 2A

Covalant bonding of immunoglobulins to amino-modified silicon.

Silicon silanized according to example 1a was modified with SPDP dissolved in 99.5% ethanol to a final concentration of 2 mM during 0.5 h in 0.1 M NaCl, 0.1 M phosphate and 1 mM ethylenediamine tetraacetate, pH 7.5 (coupling buffer). After cleaning in coupling buffer, the modified silicon surface was reduced with dithiothreitol, 50 mM, for 0.5 h. After renewed cleaning in coupling buffer, the surfaces were reacted with rabbit immunoglobulin G (IgG) in the concentrations of 1, 3, 10, 30, 100 and 300 μg/ml. The IgG had been modified with SPDP according to Carlsson, J. et al. Biochem. J., 173 (1978), 723. The modified IgG comprises an average of 3.5 SPDP/molecule after the modification. The following reference surfaces were chosen: cleaned silicon, silicon that had been exposed to the silanization procedure but without an addition of silane, amino-modified silicon, and amino-modified silicon that had been modified with SPDP but not reduced as above. For all the latter-mentioned surfaces, no covalent coupling is expected to occur. Instead, an unstable adsorption of IgG to the surfaces is obtained. No adsorption of IgG to the cleaned surfaces occurs because of the hydrophilic character of the surfaces.

Figure 3:
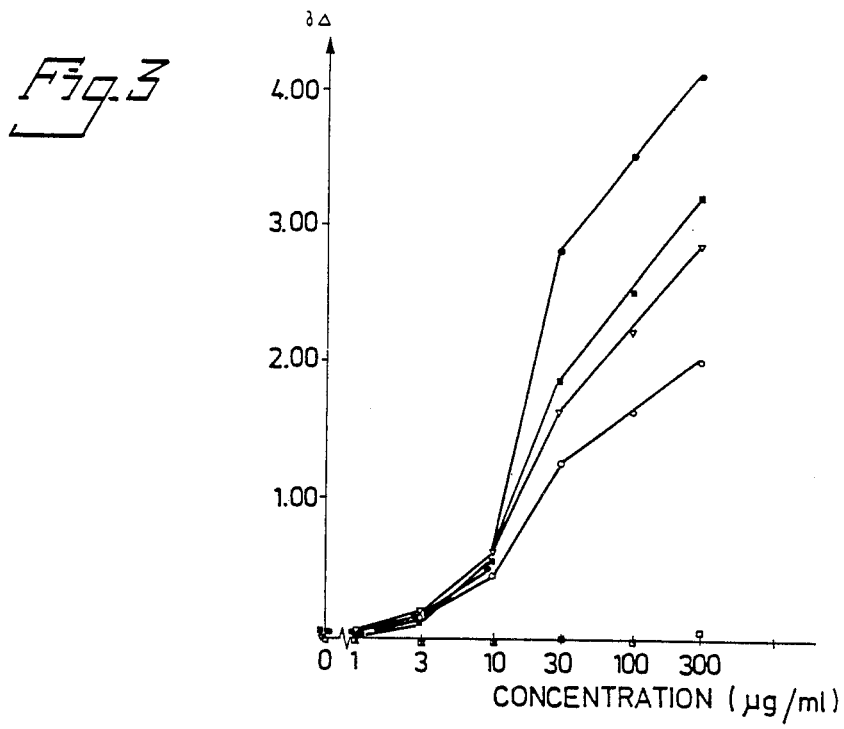
FIG. 3 is a diagram of the adsorption and coupling of immunoglobulin G from rabbit to different silicon surfaces. The meanings of the symbols used are.

The result of the bonding was evaluated by means of ellipsometry without the pieces being air-dried at any time. Here, the results are given as the change of the ellipsometric parameter $\Delta$. This parameter is for silicon approximately proportional to the amount of material per surface unit. FIG. 3 shows the change of $\Delta$ as a function of the IgG concentration. It was found that those surfaces where the covalent coupling is expected to function received the highest amount of bonded IgG. The stability of the surfaces was then tested at pH 2.5 for 30 min. Only those surfaces where covalent coupling was expected to occur showed unchanged values, while all the other surfaces lost material.

EXAMPLE 2B

Covalent bonding of Protein A and its biospecific interaction with IgG.

Pieces of aminosilanized surfaces were modified with carboxypyridyldisulfide (synthesized from dithiopyridine (Fluka) according to Carlsson, J. Et al. Biochem, J., 173 (1978), 723) 10 mM in dichloromethane comprising 10 mM dicyclohexylcarbodiimide (Aldrich) during 2 h. A base catalyst, e.g., 2,6-Lutidine, can be added which speeds up and improves the reaction. The pieces were than rinsed in dichloromethane, acetone, ethanol and water and stored in 50% ethanol. The pieces were given pyridyldisulfide groups by this modification. They were reduced with dithiothreitol according to example 2a, and then coupling was carried out for 12 h with SPDP-modified Protein A (Pharmacia Fine Chemicals), in average 3 SPDP/molecule, 100 μg/ml. After rinsing the measuring in the ellipsometer, the pieces were reacted with rabbit IgG in the concentrations of 1, 3, 10, 30, 100 and 300 ng/ml and 1, 3, 10 and 30 μg/ml. The result is shown in FIG. 4. The surfaces could be regenerated by cleaning them in a glycine buffer, pH 2.5, and the clean Protein A surface was obtained again. It could then become recoupled with IgG.

EXAMPLE 3

Silicon was silanized according to example 1b. The thiolated silicon surface was modified with SPDP 2 mM in 0.1 M NaCl, 0.1°M acetate, 1 mM EDTA pH 4.5 by means of thiolodisulfide interchanges for 1 h. After cleaning in the coupling buffer, there was added about 50 μg/ml of rabbit IgG in 0.1 M NaCl, 0.1 M phosphate, 1 mM EDTA pH 7.5 After cleaning with phosphate-buffered sodium chloride (PBS), there was added pig anti rabbit Ig purified with regard to IgG 5 μg/ML.

The coupling of protein to the silicon surface by the reaction between the introduced N-hydroxysuccinimideester and the amino groups in IgG was evaluated by means of ellipsometry. Here, a refractive index of 1.42 was estimated for the films. The film thickness can then be calculated from ellipsometry data.

|  | Si—SiO$_2$ A 189 Layer Thickness | Change in Layer Thickness |
|---|---|---|
| SPDP | 0.4 nm | +0.4 nm |
| Rabbit IgG | 3.8 nm | +3.4 nm |
| Pig anti rabbit Ig, IgG | 5.4 nm | +1.6 nm |

EXAMPLE 4A

Test of functional groups.

Thiol-containing silicon surfaces can be tested with regard to functional thiol groups by means of covalent bonding to the surfaces of 100 μl Thiopropyl Sepharose gel beads (Pharmacia Fine Chemicals, Sweden) in suspension in 0.1 M NaCl, 0.1 M phosphate, 1 mM EDTA, pH 7.5, during 1 h. By means of thioldisulfide interchange, the gel beads are bonded and cannot be rinsed away. The results can be directly and visually evaluated without aids.

TABLE 1

The specificity of thiopropyl-modified gel beads for SH- modified surfaces in comparison with other gel bead types.

|  | Unmodified gel beads | Negatively charged gel beads | Positively charged gel beads | Thiopropyl-modified gel beads |
|---|---|---|---|---|
| Surfaces only cleaned | 0 | 0 | Bonding | 0 |
| Surfaces exposed to the silanization procedure without silane | 0 | 0 | Bonding | 0 |
| Aminosilanized surfaces | 0 | 0 | 0 | 0 |
| Aminosilanized surfaces treated with SPDP | 0 | 0 | 0 | 0 |
| Aminosilanized surfaces treated with SPDP and reduced | 0 | 0 | 0 | Bonding |

Table 1 shows the specificity of Thiopropyl Sepharose for reduced, aminosilanized and SPDP-modified silicon surfaces. Unmodified gel beads (Sepharose 6B), and positively and negatively charged gel beads (DEAE and CM Sepharose, all from Pharmacia Fine Chemicals, Sweden), were chosen as controls. In the table, "0" means no bonding, while "Bonding" gives a lasting bonding of gel beads. From the table, it is evident that unmodified and negatively charged gel beads do not bond to any surface. Positively charged beads, however, bond to cleaned silicon and silicon that has been exposed to the silanization procedure without silane. This is not surprising since the oxide has negatively charged groups on its surface (Th. F. Tadros and I. Lyklema, J. Electroanal. Chem., 17 (1968), 267) at the pH that is used in the coupling process. When the ion concentration in the buffer was raised (3 M NaCl instead of 0.1 M), the bonding did not occur on said surfaces. The increase of the ion concentration did not affect the bonding of Thiopropyl Sepharose to aminosilanized surfaces that had been SPDP-modified and reduced.

EXAMPLE 4B

Stability in water solutions at different pH.

Table 2 shows the coupling of Thiopropyl Sepharose to aminosilanized surfaces after storage in a refrigerator for 2 days at a different pH. In the table, "Bonding" and "0" have the same meanings as in table 1. After storage, the pieces were thiol-modified (according to example 2a) and gel bead coupled. The controls were stored in a similar way, but not thiol-modified, which shows that the aminosilane structure has remained intact.

For those pieces that were stored at pH 12, the coupling was only partial. This is probably due to the known instability of silicon dioxide at a pH above 11.

TABLE 2

| Stability test of A-1120 silanized silion after storage for 2 days in water solutions of different pH. | | |
|---|---|---|
| SH-modified surfaces | Cleaned surfaces | Silanized surfaces without SH-modification |
| pH 1 Bonding | 0 | 0 |
| pH 3 Bonding | 0 | 0 |
| pH 5 Bonding | 0 | 0 |
| pH 6 Bonding | 0 | 0 |
| pH 7 Bonding | 0 | 0 |
| pH 9 Bonding | 0 | 0 |
| pH 10 Bonding | 0 | 0 |
| pH 11 Bonding | 0 | 0 |
| pH 12 Bonding only partially | 0 | 0 |

A similar test was also carried out the A-189 silanized surfaces (example 1b). Here, coupling of gel beads did occur only for pieces stored at pH 7.

We claim:

1. A method of silanizing a solid, plane surface so that a stable and reproducible silane layer is prepared on the surface, said silane layer having functional groups for covalent bonding of organic molecules, said method comprising the steps of:
   making said solid, plane surface free from organic and inorganic contamination, activated, hdyrophilic and reproducible by cleaning said surface in a first, basic solution comprising an oxidant, rinsing said surface in water, and then cleaning said surface in a second, acid solution comprising an oxidant;
   rinsing said solid, plane surface in water
   blow drying said solid, plane surface; and
   silanizing said solid, plane surface by vacuum distillation utilizing silane in a gas phase at a low pressure of $10^{-6}$ to 1 torr while maintaining the temperature of the solid surface between 75°–250° C.

2. A method according to claim 1, wherein the solid, plane surface is the surface of a single crystalline silicon material.

3. A method according to claim 1, which further comprises covalent bonding of organic molecules to said silanized, solid, plane surface by means of a thiol-disulfide interchange reaction, a reaction with carbodiimide or with glutaraldehyde, said solid, plane surface being provided with a functional group selected from the group consisting of thiol, succinimide, pyridyldisulfide, amino, carboxyl, epoxy, vinyl and methacryl by means of said silanizing.

4. A method according to claim 1, wherein said first, basic solution is an ammonium hydroxide solution containing hydrogen peroxide as the oxidant and said second, acid solution is a hydrochloric acid solution containing hydrogen peroxide as the oxidant.

5. A method according to claim 4, wherein said solid, plane surface is cleaned at a temperature of about 85° C.

6. A method according to claim 1, which further comprises testing said solid, plane surface, after silanizing, for the presence of functional groups by bringing said silanized, solid, plane surface together with gel beads which have been modified with organic molecules to determine whether the gel beads will bond specifically and covalently to the surface.

7. A method according to claim 6, wherein said surface having the functional group thiol by means of said silanizing, is brought together in a coupling buffer with thiopyropyl-modified gel beads, said thiopropyl-modified gel beads becoming bonded to said solid, plane surface by means of a thiol-disulphide interchange reaction.

8. A method according to claim 1, which further comprises adding a bifunctional coupling reagent to said silanized surface.

9. A method according to claim 8, wherein said bifunctional coupling reagent is N-succinimydl-3-(2-pyridyldithio)propionate.

10. A method according to claim 8, which further comprises covalent bonding of organic molecules to the bifunctional coupling reagent of said silanized surface.

11. A method according to claim 1, wherein said silanizing comprises the steps of distilling an organosilane at a pressure of $10^{-6}$ to 1 torr from a first vessel into a second vessel, said second vessel containing said cleaned and blown dry solid, plane surface, and said second vessel being kept at a pressure of $10^{-6}$ to 1 torr and a temperature of 75°–250° C.

12. A method according to claim 11, wherein the silanization pressure is $10^{-2}$ to $10^{-1}$ torr.

13. A method according to claim 11, wherein the silanization temperature is 100° to 200° C.

14. A method according to claim 11, wherein said silanizing is carried out with N-$\beta$-(aminoethyl)-$\alpha$-aminopropyltrimethoxysilane so that amino groups are introduced on said solid, plane surface.

15. A method according to claim 11, wherein said silanizing is carried out with $\alpha$-mercaptopropyltrimethoxysilane so that sulfhydryl groups are introduced on said solid, plane surface.

* * * * *

UNITED STATES PATENT AND TRADEMARK OFFICE
CERTIFICATE OF CORRECTION

PATENT NO. : 4,833,093
DATED : May 23, 1989
INVENTOR(S) : Magnus Malmqvist et al.

It is certified that error appears in the above-identified patent and that said Letters Patent is hereby corrected as shown below:

Column 12, lines 51 (Claim 14) and 55 (Claim 15), change "$\alpha$" (alpha) to --$\gamma$--(gamma).

On the title page

Please insert the third inventor's name as follows:

--Ulf Jonsson, Umea, Sweden--.

Signed and Sealed this

Twenty-first Day of November, 1989

Attest:

JEFFREY M. SAMUELS

Attesting Officer     Acting Commissioner of Patents and Trademarks